(12) United States Patent
Yamaguchi et al.

(10) Patent No.: US 6,947,146 B2
(45) Date of Patent: Sep. 20, 2005

(54) OPTICAL OBJECT IDENTIFICATION DEVICE AND PRINTING APPARATUS USING THE SAME

(75) Inventors: Akifumi Yamaguchi, Kashiba (JP); Hisakazu Sugiyama, Nara-ken (JP)

(73) Assignee: Sharp Kabushiki Kaisha, Osaka (JP)

( * ) Notice: Subject to any disclaimer, the term of this patent is extended or adjusted under 35 U.S.C. 154(b) by 103 days.

(21) Appl. No.: 10/437,233

(22) Filed: May 14, 2003

(65) Prior Publication Data

US 2003/0214656 A1 Nov. 20, 2003

(30) Foreign Application Priority Data

May 14, 2002 (JP) ........................................ 2002-138537

(51) Int. Cl.[7] .............................................. G01N 21/47
(52) U.S. Cl. ........................... 356/446; 356/71; 250/556
(58) Field of Search .......................... 356/71, 446, 600; 250/370.06, 559.11, 559.18, 556, 557; 382/135, 137, 138

(56) References Cited

U.S. PATENT DOCUMENTS

| | | | | |
|---|---|---|---|---|
| 2,827,822 A | * | 3/1958 | Timms | ........................ 356/71 |
| 3,437,823 A | * | 4/1969 | Joyce | ..................... 250/559.18 |
| 4,003,660 A | * | 1/1977 | Christie et al. | ............. 356/448 |
| 4,054,391 A | * | 10/1977 | Witte | .......................... 356/445 |
| 4,756,619 A | * | 7/1988 | Gerlinger et al. | ........... 356/446 |
| 4,919,535 A | * | 4/1990 | Hohberg et al. | ............. 356/446 |
| 5,892,239 A | * | 4/1999 | Nagase | ....................... 250/556 |
| 6,104,036 A | * | 8/2000 | Mazowiesky | ............... 250/556 |
| 6,542,248 B1 | * | 4/2003 | Schwarz | ..................... 356/600 |
| 2003/0156293 A1 | * | 8/2003 | Kazuhiko et al. | ........... 356/446 |

FOREIGN PATENT DOCUMENTS

| | | |
|---|---|---|
| JP | 10-198174 A | 7/1998 |
| JP | 2000-301805 A | 10/2000 |
| JP | 2001-180843 A | 7/2001 |

* cited by examiner

*Primary Examiner*—Michael P. Stafira
*Assistant Examiner*—Juan D Valentin, II
(74) *Attorney, Agent, or Firm*—Birch, Stewart, Kolasch & Birch, LLP

(57) ABSTRACT

An optical object identification device has a light emission element, an optical system condensing light from the light emission element, a photodetector integrated with a mask provided with a pinhole, and an identification unit for identifying a type of a measurement object by an output waveform from the photodetector.

17 Claims, 6 Drawing Sheets

(a)

(b)

OPTICAL OBJECT IDENTIFICATION DEVICE AND PRINTING APPARATUS USING THE SAME

This nonprovisional application claims priority under 35 U.S.C. § 119(a) on Patent Application No(s). 2002-138537 filed in JAPAN on May 14, 2002, which is (are) herein incorporated by reference.

BACKGROUND OF THE INVENTION

The present invention relates to an optical object identification device and a printing apparatus using the same, and more particularly to an optical object identification device for detecting information on a paper form in a noncontact way so as to improve printing quality by optimizing a quantity of ink in an ink jet printer or the like, and to a printing apparatus using the same.

In a first conventional optical object identification device, as shown in FIG. 7, a light emission element 31 and a photodetector 32 are provided so as to form a specified angle with a paper form 33. In the first conventional optical object identification device, light emitted from the light emission element 31 is reflected by the paper form 33, and then part of the reflected light is made incident on the photodetector 32. In this situation, a quantity of the light incident on the photodetector 32 differs according to a type (a surface condition) of the paper form 33. The paper form 33 is therefore identified on basis of the difference in the light quantity.

In a second conventional optical object identification device, as shown in FIG. 8, one light emission element 34 and two photodetectors 35 and 36 are provided so as to form specified angles with a plane surface of a paper form 37. In the second conventional optical object identification device, two photodetectors are provided for receiving light that is reflected spectrally and light that is reflected diffusely from the paper form 33, respectively. The paper form is identified on basis of a difference between quantities of light incident on the two photodetectors 35 and 36 which difference varies according to paper forms.

The first and second conventional optical object identification devices are composed of one light emission unit and one photodetector unit or are composed of one light emission unit and a plurality of photodetector units. Each unit is positioned so as to form a specified angle with a plane surface of a paper form, and the devices identify paper forms on basis of the difference in quantity of light reflected from the paper forms.

However, the devices have a problem in that it is difficult to identify paper forms correctly because the quantity of the reflected light varies with a quantity of light in the light emission unit, sensitivity of the photodetector units, variation in surface condition of paper forms, variation in relation among positions of the light emission unit, the photodetector units, and a paper form. Plain paper, glossy paper, photo glossy paper and OHP paper are used for paper forms. It is difficult to make identification between plain paper and glossy paper with satisfactory repeatability, while it is relatively easy to make identification other than the identification between plain paper and glossy paper.

SUMMARY OF THE INVENTION

It is therefore an object of the present invention to provide an optical object identification device that is capable of identifying types of objects such as paper forms correctly and with satisfactory repeatability and to provide a printing apparatus using the same.

In order to achieve the object, an optical object identification device of the present invention provides an optical object identification device comprising:

a light emission element;

an optical system condensing light emitted from the light emission element to cast the light on a measurement object moving in a specified direction and thereby to form a light spot having a specified spot diameter on the measurement object, and condensing light reflected from at least an area of the light spot;

a mask provided with a pinhole passing at least part of the reflected light condensed by the optical system;

a photodetector on which the light passed through the pinhole is incident; and an identification unit for identifying a type of the measurement object on basis of an output waveform from the photodetector.

Waveforms outputted from the photodetector differ according to types of the measurement objects, that is, surface conditions of the measurement objects. In the configuration of the present invention, the type of the measurement object is correctly identified with satisfactory repeatability by an output waveform from the photodetector through processing in an electric circuitry.

In one embodiment of the present invention, the light emission element is a semiconductor laser.

Since laser light is efficiently condensed by the lenses of the optical system, it is possible to obtain a sufficient quantity of light that the photodetector requires for detection from the light reflected from the measurement object.

In one embodiment of the present invention, the light cast on the measurement object is parallel light having an axis generally perpendicular to a plane surface of the measurement object.

In the case that the light cast on the measurement object is parallel, a quantity of the reflected light incident on the photodetector from the measurement object does not change. Thus, signal-to-noise ratio does not decrease even if the distance to the measurement object is changed.

In one embodiment of the present invention, the mask having a pinhole is integrally provided on a light receiving surface of the photodetector.

In one embodiment of the present invention, the pinhole and the photodetector are capable of moving relatively to the optical system.

Since the photodetector integrated with the pin hole can move relatively to the optical system, it is easy to return to the original state in the quantity of light incident on the photodetector when the measurement object is moved in the direction of the axis of emission light in the optical object identification device. Then, the distance between the measurement object and the optical object identification device can be detected based on a moving quantity of the photodetector.

In one embodiment of the present invention, a diameter of the pinhole is in a range from 10 $\mu$m to 50 $\mu$m.

The diameter of the pinhole is in a range from 10 $\mu$m to 50 $\mu$m so that surface condition of the measurement object may be read and that an appropriate quantity of light may be obtained.

If the diameter of the pinhole is larger than 50 $\mu$m, the surface condition is obtained by light reflected from an excessively wide area on the measurement object. As a result, information on projections and depressions on the surface is uniformlized, so that difference in positions becomes too small to detect a true surface condition. On the other hand, if the diameter of the pinhole is smaller than 10 μm, though the surface condition can be read precisely, sufficient signal cannot be obtained due to lack of the light quantity. In other words, sizes of the pinhole out of the range from 10 μm to 50 μm make it difficult to identify the type of the measurement object.

The present invention provides an optical object identification device comprising:

a light emission element;

an optical system condensing light emitted from the light emission element to cast parallel light on a measurement object moving in a specified direction, the parallel light having an axis generally perpendicular to a plane surface of the measurement object, and thereby to form a light spot having a specified spot diameter on the measurement object, and that condensing light reflected from the light spot;

a two-division photodetector on which the reflected light condensed by the optical system is incident; and an identification unit for identifying a type of the measurement object on basis of an output waveform from the two-division photodetector.

In the present invention, instead of the photodetector together with the pinhole, a two-division photodetector, which has a light receiving surface divided into two areas, is used for detecting the distance between the measurement object and the optical object identification device. A change in the distance between the measurement object and the device causes changes in respective quantities of light incident on both light receiving surfaces. Therefore, the distance can be detected based on a difference or a ratio between both quantities of light.

The present invention provides an optical object identification device comprising:

a light emission element;

an optical system condensing light emitted from the light emission element to cast parallel light on a measurement object moving in a specified direction, the parallel light having an axis generally perpendicular to a plane surface of the measurement object, and thereby to form a light spot having a specified spot diameter on the measurement object, and condensing light reflected from the light spot;

a position sensitive photodetector on which the reflected light condensed by the optical system is incident; and an identification unit for identifying a type of the measurement object on basis of an output waveform from the position sensitive photodetector.

In the present invention, instead of the photodetector together with the pinhole or the two-division photodetector, a position sensitive device (PSD) is used which has two output values varying according to positions of a light spot.

In one embodiment of the present invention, a beam diameter of the parallel light is 50 μm or less.

The parallel light having a beam diameter 50 μm or less, which is vertically cast on the measurement object, the beam diameter is unchanged even if the measurement object shifts in the direction of the axis of the emission light. Therefore, there is no necessity to confine light by the pinhole because the light has reflected only from an area on the measurement object having this beam diameter. If the beam diameter of the parallel light is larger than 50 μm, an irradiated area on the measurement object is also larger than 50 μm in diameter. This means that the irradiated area is considerably large relative to widths of projections or depressions on the surface of the measurement object. As a result, as is above mentioned, information on the projections and depressions is uniformlized. Thus, an amplitude of an output waveform from the photodetector is reduced during movement of the measurement object, so that signal-to-noise ratio decreases.

In one embodiment of the present invention, the optical object identification device further comprises a case having a guide that guides the measurement object so as to press the measurement object against a reference surface.

According to this embodiment, thickness of the measurement object can be detected by pressing the measurement object against the reference surface in addition to that the distance between the measurement object and the sensor can be detected by perpendicularly casting light on the measurement object as described above.

The present invention provides a printing apparatus comprising:

the optical object identification device as claimed in claim 1; and an ink control unit that controls a quantity of ink on basis of information on the measurement object that is identified with use of the optical object identification device.

A printing apparatus can obtain high quality image by controlling a quantity of ink with use of an ink control unit based on information such as type or thickness of the measurement object that the optical object identification device determines.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1A:
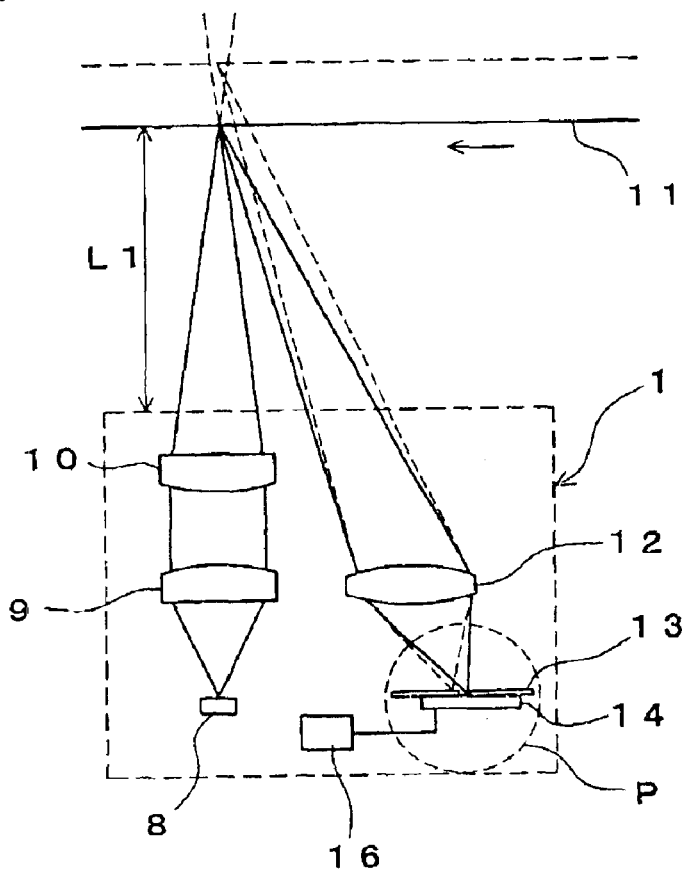
FIG. 1A is a schematic configuration of an optical object identification device in accordance with a first embodiment of the invention.

Hereinbelow, an optical object identification device of the invention and a printing apparatus using the same will be described in detail with reference to embodiments shown in the drawings.

First Embodiment

Figure 1B:
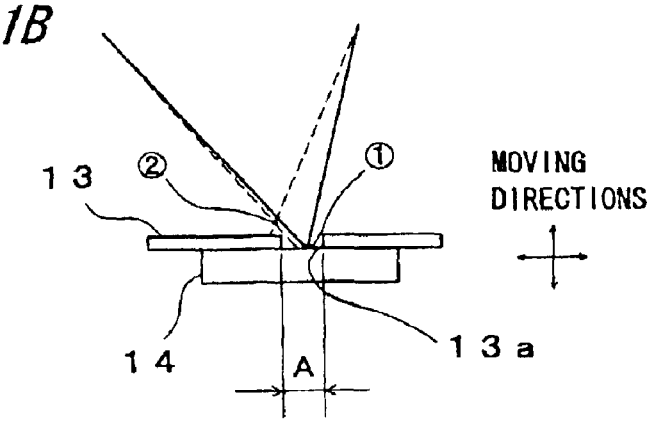
FIG. 1B is a partial enlarged view of FIG. 1A.

FIG. 1A is a schematic configuration of an optical object identification device in accordance with a first embodiment of the invention. FIG. 1B is a partial enlarged view of FIG. 1A. In FIGS. 1A and 1B, reference numeral 8 denotes a light emission element (preferably, a semiconductor laser), numeral 9 denotes a collimating lens, numeral 10 denotes an objective lens, numeral 11 denotes a measurement object, numeral 12 denotes a light receiving lens, numeral 13 denotes a mask in which a pinhole 13a is provided, numeral 14 denotes a photodetector, and numeral 16 denotes an identification unit that receives signal from the photodetector 14 and that identifies a type of the measurement object 11.

The collimating lens 9, the objective lens 10, and the light receiving lens 12 configure an optical system that condenses light emitted from the light emission element 8, casts the light on the measurement object 11 that is moving in a specified direction, and thereby forms a light spot having a specified spot diameter on the measurement object 11 and that condenses light reflected from at least an area of the light spot. A sensor section 1 is composed of the light emission element 8, the collimating lens 9, the objective lens 10, the light receiving lens 12, the pinhole 13a, the photodetector 14, and the identification unit 16.

As shown in FIG. 1, the optical object identification device of the first embodiment collimates light emitted from the light emission element 8 by the collimating lens 9. Thereafter, the optical object identification device casts the light through the objective lens 10 onto the measurement object that is moving in the specified direction. The light is so cast as to make an axis of the light generally perpendicular to the measurement object 11, and to form a light spot having a specified spot diameter on the measurement object 11. Subsequently, the device condenses light reflected from the light spot on the measurement object 11 by the light receiving lens 12 and makes the light incident on the photodetector 14 through the pinhole 13a. The light incident on the photodetector 14 is limited only to light condensed by the light receiving lens 12 and passed through the pinhole 13a out of the light reflected by the measurement object 11. This means that light from a partial area or the whole area of the light spot on the measurement object 11 is made incident on a light receiving region of the photodetector 14 according to a size of the pinhole 13a.

When the measurement object 11 is in a position shown by a solid line in FIG. 1, the diameter of the spot formed on the measurement object 11 is minimized. Light reflected from the whole area of the light spot with the minimized spot diameter is condensed by the light receiving lens 12 and is made incident on the photodetector 14 through the pinhole 13a. With shift of the measurement object 11 from the position shown by the solid line to a position shown by a broken line, the diameter of the spot formed on the measurement object 11 increases so that light reflected from a partial area of the enlarged light spot is condensed by the light receiving lens 12 and is made incident on the photodetector 14 through the pinhole 13a.

When the measurement object 11 is shifted in the direction of the axis of the light cast from the sensor section 1, the diameter of the spot formed on the measurement object 11 is changed. In other words, an area irradiated with the light is changed. Therefore, light from only a specified area of the light spot on the measurement object 11 is incident on the photodetector 14 on condition that the pinhole 13a and the photodetector 14 are moved relatively to the optical system so as to maximize a quantity of light passing through the pinhole 13a. Thereby, a surface condition of the measurement object 11 can be read with an accuracy as high as that prior to the shift of the measurement object 11. As for moving directions in this operation, a vertical arrow in FIG. 1B represents the light axis direction of the light cast on the measurement object 11, and a horizontal arrow represents the direction in which the measurement object 11 moves.

In the embodiment, a size A of the pinhole 13a is required to be about 10 μm to 50 μm in order that the surface condition of the measurement object 11 may be read and in order that an appropriate quantity of light may be obtained. If the size A of the pinhole 13a is too large, the surface condition is supposed to be read on basis of reflected light from a wide area on the measurement object 11. As a result, information on the surface condition is averaged so as to differ little according to positions of the measurement object and thus a true surface condition cannot be detected. If the size A of the pinhole 13a is small, the surface condition can be read precisely. If the size is too small, however, sufficient signal cannot be obtained because of an insufficient quantity of light.

The pinhole 13a is provided in the metal mask 13 that is formed on a light receiving surface of the photodetector 14 in the semiconductor fabricating process. Preferably, the mask 13 having the pinhole 13a and the photodetector 14 are integrally formed in structure.

When the measurement object 11 is shifted in the direction of the light axis on the light emission side of the device, in this structure, both the pinhole 13a and the photodetector 14 also move so as to maximize a quantity of light reflected from the measurement object 11, passing through the pinhole 13a and being incident on the photodetector 14 (as shown in FIG. 1, a position (1) is so moved to a position (2) as to maximize the quantity of light incident on the light receiving region). Accordingly, a distance L1 between the measurement object 11 and the sensor section 1 can be detected based on a direction and a quantity of the movement.

Figure 2:
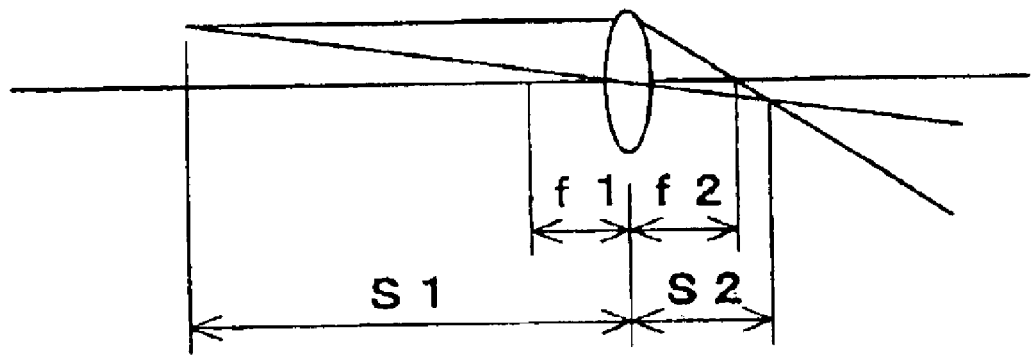
FIG. 2 is a diagram for illustrating a principle of detection of a distance between a measurement object and a sensor section by the optical object identification device.

The axis of the light cast on the measurement object 11 is generally perpendicular to the plane surface of the measurement object 11. In an optical system shown in FIG. 2, the following lens imaging formula is held.

$$f1/S1 + f2/S2 = 1$$

wherein S1 corresponds to a distance between the measurement object 11 and the light receiving lens 12, S2 corresponds to a distance between the light receiving lens 12 and the photodetector 14, and f1 and f2 represent focal lengths. The lens imaging formula means that a change in S1 relates to a change in S2. Therefore, the distance between the measurement object 11 and the sensor section 1 can be detected by the change in S2.

The optical object identification device having the above configuration can correctly identify with satisfactory repeatability, a type of the measurement object 11, such as plain paper, glossy paper, photo glossy paper and OHP paper. Also, the optical object identification device can detect the distance L1 between the measurement object 11 and the sensor section 1 of the device.

In the case of using a semiconductor laser as the light emission element 8, laser light is efficiently condensed by the lenses. Thereby, a quantity of light required by the photodetector 14 for detection of signal can be obtained from the light reflected from the light spot on the measurement object 11.

A shape of the light spot on the measurement object 11 does not change when using parallel light having an axis generally perpendicular to the plane surface of the measurement object 11 as light cast on the measurement object 11 moving in the specified direction. The shape of the light spot on the measurement object 11 does not change even if the distance between the measurement object 11 and the sensor section 1 changes due to variation in position of the measurement object 11. As a result, light incident on the photodetector 14 is light reflected from an area having always the same size on the measurement object 11. Thus, an output of the photodetector 14 is prevented from changing, so that the measurement object 11 can be identified correctly.

As mentioned above, the pinhole 13a is provided in the mask 13 on the light receiving surface of the photodetector 14 to be integrated with the photodetector 14. Therefore, the size and position of the pinhole 13a can be set with a high accuracy during the semiconductor process. Thereby, a cost of the device is reduced in comparison with that of a device where the pinhole is provided in a separate member.

The pinhole 13a and the photodetector 14 are moved relatively to the optical system of the sensor section 1 so that a quantity of light incident on the photodetector 14 is maximized. Therefore, the distance L1 between the measurement object 11 and the sensor section 1 is detected on the basis of direction and a quantity of their movement.

When setting the diameter of the pinhole 13a in a range from 10 $\mu$m to 50 $\mu$m, the surface condition of the measurement object 11 can be correctly read, and also an appropriate quantity of light can be obtained. As a result, an output waveform appropriate for signal processing can be obtained and the type of the measurement object 11 can be identified with satisfactory repeatability.

Second Embodiment

Figure 3A:
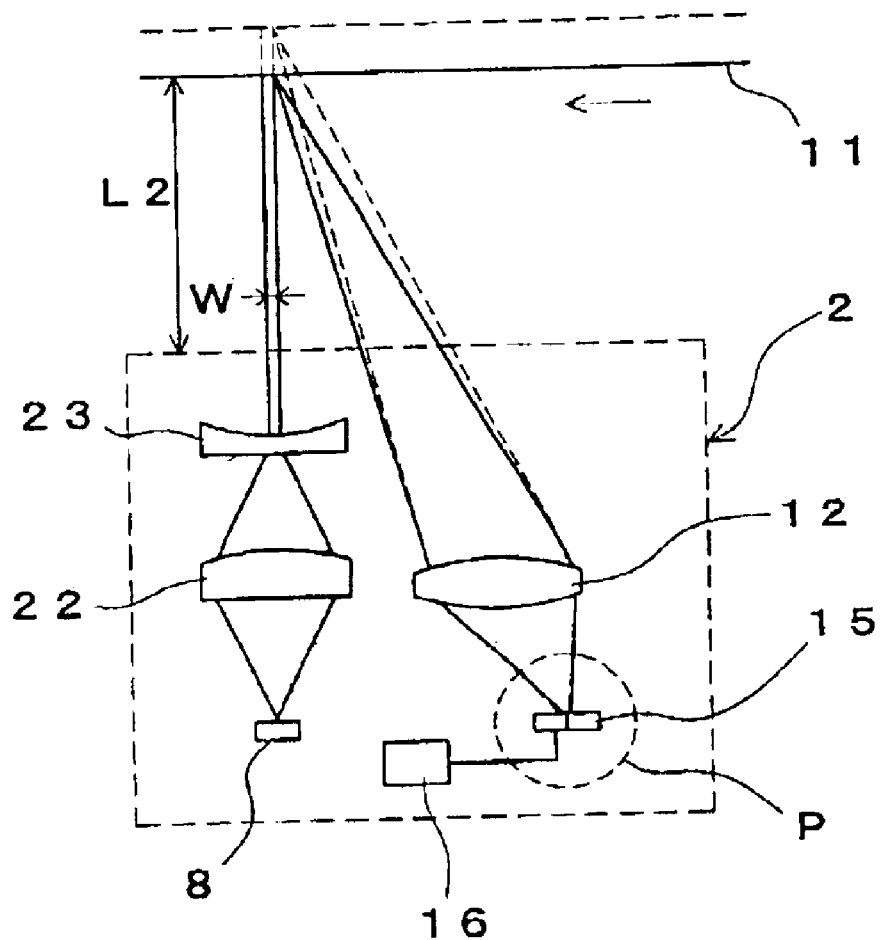
FIG. 3A is a schematic configuration of an optical object identification device in accordance with a second embodiment of the invention.
Figure 3B:
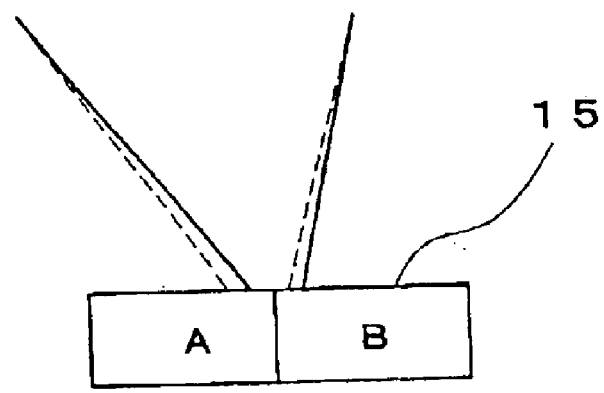
FIG. 3B is a partial enlarged view of FIG. 3A.

FIG. 3A is a schematic configuration of an optical object identification device in accordance with a second embodiment of the invention. FIG. 3B is a partial enlarged view of FIG. 3A. In FIG. 3A, reference numeral 8 denotes a light emission element (preferably, a semiconductor laser), numeral 22 denotes a convex lens, numeral 23 denotes a concave lens, numeral 11 denotes a measurement object, numeral 12 denotes a light receiving lens, numeral 15 denotes a two-division photodetector having a light receiving surface divided into two areas, and numeral 16 denotes an identification unit that receives signal from the photodetector 15 and that identifies a type of the measurement object 11. The convex lens 22, the concave lens 23, and the light receiving lens 12 configure an optical system that condenses light emitted from the light is emission element 8, casts parallel light on the measurement object 11 moving in a specified direction, the parallel light having an axis generally perpendicular to a plane surface of the measurement object 11, and thereby forms a light spot having a specified spot diameter on the measurement object 11 and that condenses light reflected from the light spot. A sensor section 2 is composed of the light emission element 8, the convex lens 22, the concave lens 23, the light receiving lens 12, the two-division photodetector 15, and the identification unit 16. The light receiving surfaces A and B of the two-division photodetector 15 are placed so as to be generally perpendicular to the axis of the light cast on the measurement object 11 and so as to extend along the direction in which the measurement object 11 moves.

As shown in FIGS. 3A and 3B, light emitted from the light emission element 8 is condensed by the convex lens 22 and, subsequently, parallel light is produced by the concave lens 23. The parallel light is cast on the measurement object 11 vertically in general with respect to the measurement object 11. When a beam diameter W is about 50 $\mu$m or smaller, there is no necessity to confine the light by the pinhole as in the first embodiment. This is because the reflection from the measurement object 11 occurs only in an area corresponding to the beam diameter even if the measurement object 11 shifts in the direction of the axis of the light on the light emission side in the device. In this arrangement, the two-division photodetector 15 is fixed without being moved relatively to other components, for detecting a distance L2 between the measurement object 11 and the sensor section 2. In principle, a lower limit of the beam diameter of the parallel light is several micrometers that is a limit of focusing by a lens.

A change in the distance L2 between the measurement object 11 and the sensor section 2 causes changes in quantities of light incident on the light receiving surfaces A and B. The distance L2 can be detected on basis of a difference (or a ratio) between the quantities. In FIGS. 3A and 3B, when the distance L2 between the measurement object 11 and the sensor section 2 is increased as shown by broken lines, a quantity of light incident on the light receiving surface A becomes greater than a quantity of light incident on the light receiving surface B.

The optical object identification device having the above configuration can correctly identify a type of such an object as plain paper, glossy paper, photo glossy paper and OHP paper with satisfactory repeatability. The optical object identification device can also detect the distance L2 between the measurement object and the sensor section of the device.

In the case of using a semiconductor laser as the light emission element 8, laser light is efficiently condensed by the lenses. Thereby, a quantity of light required by the photodetector 14 for detection of signal can be obtained from the light reflected from the light spot on the measurement object 11.

A shape of the light spot on the measurement object 11 does not change when using parallel light having an axis generally perpendicular to the plane surface of the measurement object 11 as light cast on the measurement object 11 moving in the specified direction. The shape of the light spot on the measurement object 11 does not change even if the distance L2 between the measurement object 11 and the sensor section 1 changes due to variation in position of the measurement object 11. As a result, light incident on the photodetector 15 is light reflected from an area having always the same size on the measurement object 11. Thus, an output of the photodetector 15 is prevented from changing, so that the measurement object 11 can be identified correctly.

The two-division photodetector 15 is provided as a photodetector so that no movement of the photodetector in relation to other components is required and that formation of a pinhole is unnecessary. As a result, design and manufacture of the device are facilitated and a cost of the device is reduced.

Figure 4:
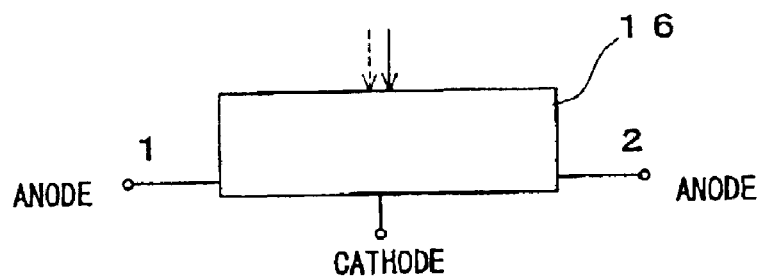
FIG. 4 is a schematic diagram of a position sensitive photodetector of the optical object identification device.

A position sensitive device 16 shown in FIG. 4 may be used instead of the two-division photodetector 15. In the position sensitive device 16, two output values vary according to positions of a light spot. When a center of the light spot is shifted from a solid line arrow to a broken line arrow or vice versa as shown in FIG. 4, there occurs a change in output from an anode 1 and an anode 2. Therefore, a position can be detected (in this example, the distance L2 between the measurement object 11 and the sensor section 2 can be detected). This configuration eliminates the necessity for moving the position sensitive device relatively to other components and the necessity for the pinhole. As a result, design and manufacture of the device are facilitated and a cost of the device is reduced.

The beam diameter of the parallel light is about 50 μm or smaller, which eliminates the necessity to confine the light by the pinhole and the necessity to consider accuracy in position and size of the pinhole. Thus design and manufacture of the device are facilitated.

Third Embodiment

Figure 5A:
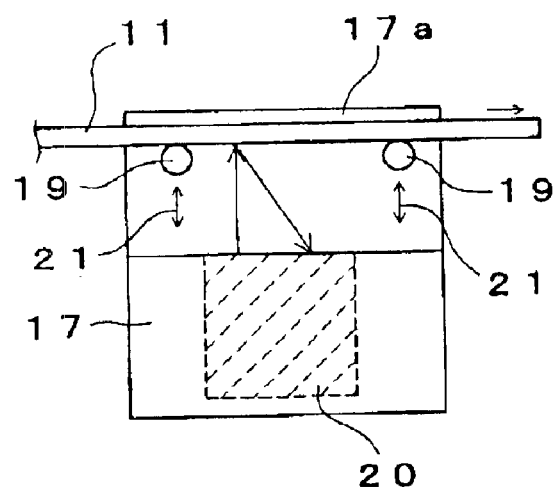
FIG. 5A is a front view illustrating a schematic configuration of a main part of an optical object identification device in accordance with a third embodiment of the invention.
Figure 5B:
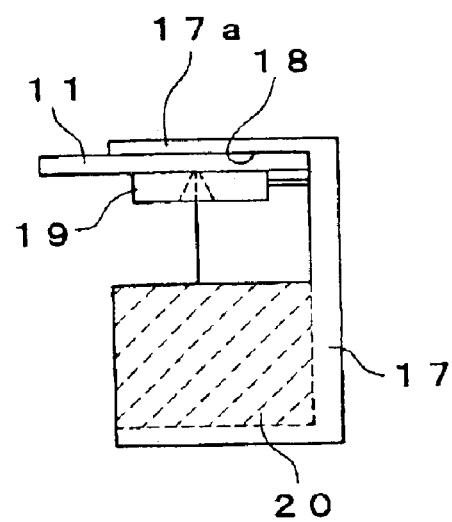
FIG. 5B is a side view of the optical object identification device.

FIG. 5A is a front view illustrating a schematic configuration of a main part of an optical object identification device in accordance with a third embodiment of the invention. FIG. 5B is a side view of the optical object identification device. In FIGS. 5A and 5B, reference numeral 11 denotes a measurement object, numeral 17 denotes a case having a guide 17a that guides the measurement object 11, numeral 18 denotes a reference surface of the guide 17a that guides the measurement object 11, numerals 19 denote rollers that press the measurement object 11 against the reference surface 18, and numeral 20 denotes a sensor section. The sensor section 20 has the same configuration as either the sensor section 1 of the optical object identification device in the first embodiment or the sensor section 2 thereof in the second embodiment.

In the optical object identification device, as shown in FIGS. 5A and 5B, the rollers 19 press the measurement object 11 against the reference surface 18. The rollers 19 are capable of moving in directions of arrows 21 in the drawings according to a thickness of the measurement object 11. Irradiation light from the sensor section 20 perpendicularly falls on a plane surface of the measurement object 11 pressed against the reference surface 18. A distance between the measurement object 11 and the sensor section 20 can be detected in the same manner as described in the first and second embodiments. Accordingly, a thickness of the measurement object 11 can be detected with the measurement object 11 pressed against the reference surface 18. For example, a distance A between the measurement object and the sensor section 20 is previously measured while a reference measurement object having a specified thickness t1 is pressed against the reference surface 18. Subsequently, a distance B between the measurement object 11 and the sensor section 20 is measured while a measurement object 11 is pressed against the reference surface 18. Then, a thickness t2 of the measurement object 11 is determined from the following equation.

$$t2 = t1 + (A - B)$$

When the measurement object 11 moves under the above configuration, output waveforms from a photodetector of the sensor section 20 differ according to types of the measurement object 11 such ash surface conditions of the measurement object. More specifically, mean values, amplitudes and periods of the output differ among plain paper, glossy paper, photo glossy paper and OHP paper. The difference in output signal from the photodetector is processed by means of electric circuitry, so that the type of the measurement object 11 can be identified in addition to detecting the thickness of the measurement object 11.

Fourth Embodiment

Figure 6:
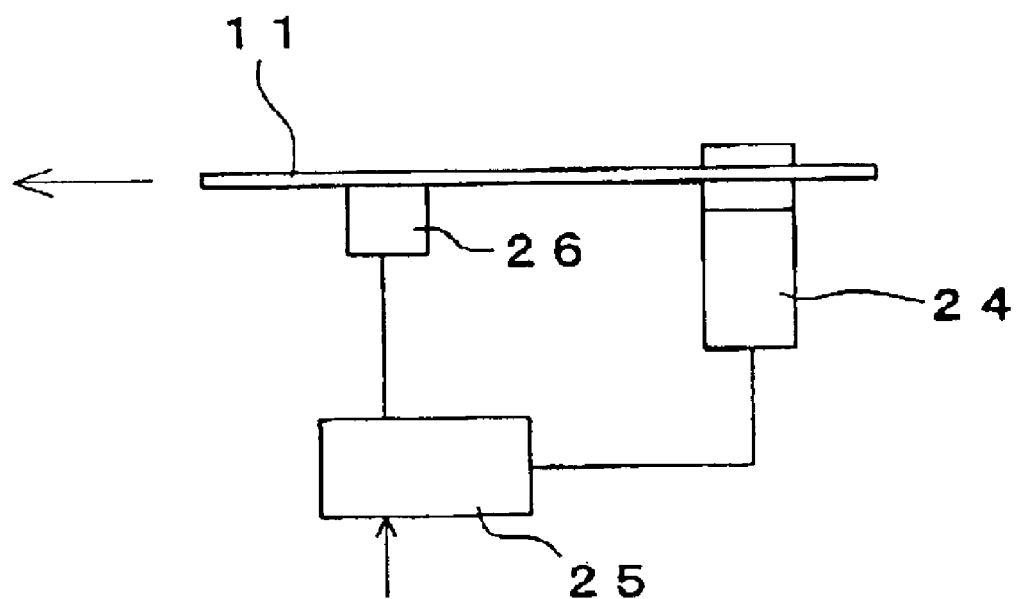
FIG. 6 is a schematic configuration of an optical object identification device in accordance with a fourth embodiment of the invention.
Figure 7:
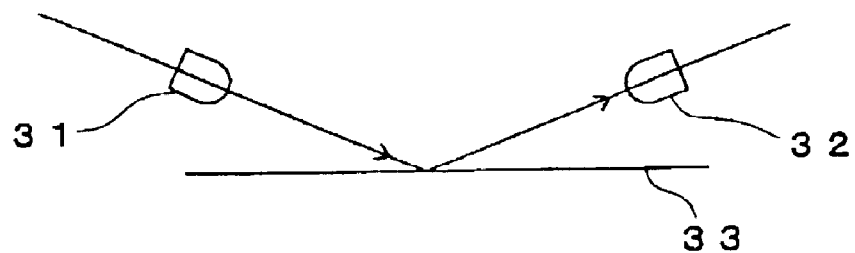
FIG. 7 is a pattern diagram of a first conventional optical object identification device.
Figure 8:
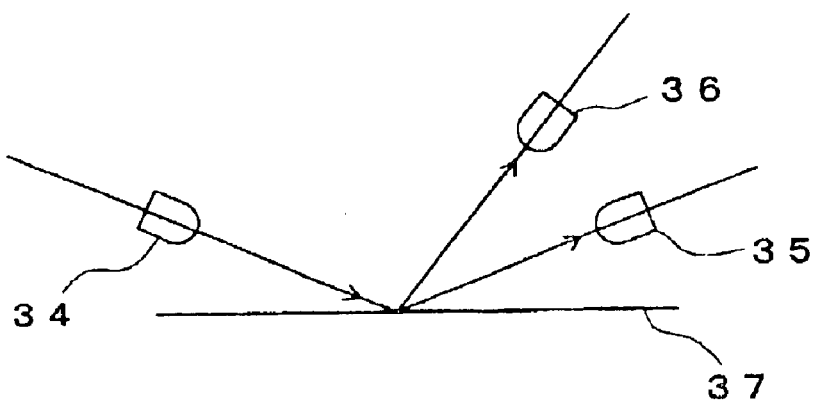
FIG. 8 is a pattern diagram of a second conventional optical object identification device.

FIG. 6 is a schematic configuration of a printing apparatus using an optical object identification device in accordance with a fourth embodiment of the invention. Reference numeral 24 denotes the optical object identification device of the third embodiment, numeral 25 denotes an ink control section that receives signal from the optical object identification device 24, and numeral 26 denotes a print head that performs printing on basis of control signal from the ink control section 25. As shown in FIG. 6, the type and thickness of the measurement object 11 are determined with use of the optical object identification device 24. Information on the type and thickness of the measurement object 11 is fed back to the ink control section 25. A quantity of ink in the print head 26 is thereby optimized, so that a high-image-quality printing apparatus is obtained.

In the first through fourth embodiments, types of recording media such as paper form are identified as an example of the measurement object. However, the measurement object has only to be an object having a plane surface.

In the fourth embodiment, the printing apparatus using the optical object identification device has been described. However, the optical object identification device of the invention may be applied not only to printing apparatus but broadly to any apparatus for identifying an object having a plane surface.

As is evident from the above description, the optical object identification device of the invention correctly identifies the type of a measurement object such as plain paper, glossy paper, photo glossy paper and OHP paper with satisfactory repeatability, and also detects the distance between the measurement object and the device.

The printing apparatus of the invention feeds back to the ink control section information such as type and thickness about the measurement object that has been determined with use of the optical object identification device. A quantity of ink can thereby be optimized, so that high-image-quality printing can be achieved.

The invention being thus described, it will be obvious that the invention may be varied in many ways. Such variations are not to be regarded as a departure from the spirit and scope of the invention, and all such modifications as would be obvious to one skilled in the art are intended to be included within the scope of the following claims.

What is claimed is:

1. An optical object identification device comprising:
    a light emission element;
    an optical system condensing light emitted from the light emission element to cast the light on a measurement object moving in a specified direction and thereby to form a light spot having a specified spot diameter on the measurement object, and condensing light reflected from at least an area of the light spot;
    a mask provided with a pinhole passing at least part of the reflected light condensed by the optical system;
    a photodetector on which the light passed through the pinhole is incident; and
    an identification unit for identifying a type of the measurement object on basis of an output waveform from the photodetector.

2. The optical object identification device as claimed in claim 1, wherein
    the light emission element is a semiconductor laser.

3. The optical object identification device as claimed in claim 1, wherein
    the light cast on the measurement object is parallel light having an axis generally perpendicular to a plane surface of the measurement object.

4. The optical object identification device as claimed in claim 1, wherein
    the mask is integrally provided on a light receiving surface of the photodetector.

5. The optical object identification device as claimed in claim 1, wherein
    the pinhole and the photodetector are capable of moving relatively to the optical system.

6. The optical object identification device as claimed in claim 1, wherein
a diameter of the pinhole is in a range from 10 μm to 50 μm.

7. An optical object identification device comprising:
a light emission element;
an optical system condensing light emitted from the light emission element to cast parallel light on a measurement object moving in a specified direction, the parallel light having an axis generally perpendicular to a plane surface of the measurement object, thereby to form a light spot having a specified spot diameter on the measurement object, and condensing light reflected from the light spot;
a two-division photodetector on which the reflected light condensed by the optical system is incident; and
an identification unit for identifying a type of the measurement object on basis of an output waveform from the two-division photodetector.

8. An optical object identification device comprising:
a light emission element;
an optical system condensing light emitted from the light emission element to cast parallel light on a measurement object moving in a specified direction, the parallel light having an axis generally perpendicular to a plane surface of the measurement object, thereby to form a light spot having a specified spot diameter on the measurement object, and condensing light reflected from the light spot;
a position sensitive photodetector on which the reflected light condensed by the optical system is incident; and
an identification unit for identifying a type of the measurement object on basis of an output waveform from the position sensitive photodetector.

9. The optical object identification device as claimed in claim 3, wherein
a beam diameter of the parallel light is 50 μm or less.

10. The optical object identification device as claimed in claim 7, wherein
a beam diameter of the parallel light is 50 μm or less.

11. The optical object identification device as claimed in claim 8, wherein
a beam diameter of the parallel light is 50 μm or less.

12. The optical object identification device as claimed in claim 1, further comprising:
a case having a guide that guides the measurement object so as to press the measurement object against a reference surface.

13. The optical object identification device as claimed in claim 7, further comprising:
a case having a guide that guides the measurement object so as to press the measurement object against a reference surface.

14. The optical object identification device as claimed in claim 8, further comprising:
a case having a guide that guides the measurement object so as to press the measurement object against a reference surface.

15. A printing apparatus comprising:
the optical object identification device as claimed in claim 1; and
an ink control unit that controls a quantity of ink on basis of information on the measurement object that is identified with use of the optical object identification device.

16. A printing apparatus comprising:
the optical object identification device as claimed in claim 7; and
an ink control unit that controls a quantity of ink on basis of information on the measurement object that is identified with use of the optical object identification device.

17. A printing apparatus comprising:
the optical object identification device as claimed in claim 8; and
an ink control unit that controls a quantity of ink on basis of information on the measurement object that is identified with use of the optical object identification device.

* * * * *